United States Patent [19]

Swonger et al.

[11] 4,210,899
[45] Jul. 1, 1980

[54] FINGERPRINT-BASED ACCESS CONTROL AND IDENTIFICATION APPARATUS

[75] Inventors: Claron W. Swonger, Elma, N.Y.; Dan M. Bowers, Fairfield, Conn.; Robert M. Stock, Severna Park, Md.

[73] Assignee: Fingermatrix, Inc., North White Plains, N.Y.

[21] Appl. No.: 855,043

[22] Filed: Nov. 25, 1977

Related U.S. Application Data

[63] Continuation of Ser. No. 589,287, Jun. 23, 1975, abandoned.

[51] Int. Cl.² ............................................. G06K 9/12
[52] U.S. Cl. ........................... 340/146.3 E; 340/149 R
[58] Field of Search .............. 340/146.3 E, 146.3 H, 340/146.3 AC, 149 R, 149 A

[56] References Cited

U.S. PATENT DOCUMENTS

| | | | |
|---|---|---|---|
| 3,676,847 | 7/1972 | Partin | 340/146.3 AC |
| 3,735,349 | 5/1973 | Beun et al. | 340/146.3 H |
| 3,771,129 | 11/1973 | McMahon | 340/146.3 E |
| 3,859,633 | 1/1975 | Ho et al. | 340/146.3 E |
| 3,940,795 | 2/1976 | Lemelson | 340/149 A |

*Primary Examiner*—Joseph M. Thesz
*Attorney, Agent, or Firm*—McAulay, Fields, Fisher & Goldstein

[57] ABSTRACT

A system including electronic, mechanical and optical mechanisms which enable the system to: "read" a human fingerprint directly from a human finger; convert the ridge-valley pattern of that fingerprint into an electronic representation; transmit the electronic representation to a centralized location where image processing computing equipment can locate and extract the distinctive characteristics or minutiae of the fingerprint; compare the minutiae with minutiae previously recorded from the fingerprints of persons whom the system is responsible for identifying; determine whether the identity of the person whose fingerprint is read is known, and, if known, whether or not the person is authorized to enter the portal equipped with this system, or to otherwise act; and, to transmit a signal to the terminal and/or portal regarding the system's decision.

4 Claims, 4 Drawing Figures

FINGERPRINT-BASED ACCESS CONTROL AND IDENTIFICATION APPARATUS

This is a continuation of application Ser. No. 589,287, filed June 23, 1975, now abandoned.

Increasing security problems are becoming a noticeable part of modern life; security was once primarily the preserve of classified government installations, but increasing losses and calamities have forced the review of security equipment and procedures by government and industry. Cargo losses and the theft of corporate secrets cost industry billions of dollars annually. Public safety is endangered by the ability of intruders to plant bombs in places such as aircraft and buildings. Computerized records and even the computers themselves, are attacked and destroyed.

Access control and personnel identification are becoming tremendous problems, and will be the object of significant expenditures by organizations needing to identify employees, vendors, etc., who are to be allowed access to plants, computer rooms, vaults, baggage areas, etc. The ultimate method of personal identification is not a card which can be lost, loaned or stolen, nor a number code which can be told or purloined; but an unchangeable, non-transferable and indisputably unique characteristic of the person himself, his fingerprint.

It is an object of this invention to provide a fingerprint-based access control system which can read a human fingerprint directly from a human finger.

It is an additional object of this invention to provide a system for providing a limited access to areas by individuals by identifying them through their fingerprints.

It is a further object of this invention to record timekeeping and payroll data as well as to log personnel entry/exit to specific areas.

It is an additional object of this invention to provide a positive identification system for banking and credit card transactions.

It is an additional object of this invention to extract and use the unique personal characteristics of fingerprints which are derived and used by law enforcement agencies so that data on individuals attempting an unauthorized access can be forwarded to the agencies for action.

It is an additional object of this invention to provide an identification system in which the data against which an individuals's characteristics are compared is not accessible to the individual to prevent forgery and loss or theft of said data.

It is a still further object of this invention to provide a fingerprint-based access control system which is readily encoded to cover changes in personnel. These objects, and others as will become apparent hereinafter, are accomplished by the present invention.

The present invention is directed to a system for providing a limited access to physical space, information, services, etc. by individuals by identifying them through their fingerprints. If the system determines that the individual's fingerprint characteristics match with the characteristics on file for the alleged (keyed-in) identity number, and if that identity is authorized access under the registered conditions, then an affirmative action such as opening a door or unlocking a computer terminal will be taken. The individual approaches the identification terminal, inserts a card or keys in a number as identification of who he alleges to be, and then puts his previously designated finger onto the surface of a fingerprint reader which scans the fingerprint and transmits an enhanced representation of the image to a central computer or "central station".

At the central station, the fingerprint data is processed in order to determine its minutiae characteristics (ridge endings and ridge bifurcations) and a comparison is made against the minutiae characteristics on file for the alleged identity. Other information on file for the individual will include data or what areas, terminals or doors he has access to, time periods of access, and/or other control information. A signal is returned to the terminal designating if he is allowed access, or asking for another reading if no match is made. Subsequent unsuccessful attempts may result in an alarm or other remedial action.

A number of advantages are offered by the use of the present invention. Positive identification of a person, rather than a card, is made through the person's fingerprints which are the only widely accepted form of personal identification. No inked impression is taken since there is a direct reading and digitizing of minutiae. Since a card is not required, the system is secure and the response time can be on the order of 2 seconds. Additionally, the system offers an individualized access list including permissible access times for each terminal or portal, provides a data log of personnel activity and requires no additional or special equipment for encoding new personnel into the file since standard terminals are used. There is a central control and monitoring of security and a selectable response to attempts at defeating the system.

The system of the present invention may be adapted to a number of installations each having their specific requirements. A system may have a single terminal or many, and the terminals may be local to the centralized equipment or remote from it. Transmission from the terminals to the central system may be through a direct wire, telephone, or other data transmission system. The system may be constructed so as to monitor an unlimited number of persons, and the response time of the system will depend upon the number of terminals used and their total inquiry rate and whether or not telephone line transmission or other low bandwidth communication lines are required.

Typical access control applications for the present invention would include: computer centers; radioactive or biological danger areas; controlled experiments; information storage areas; airport maintenance and freight areas; hospital closed areas and drug storage areas; apartment houses and office buildings after hours; safe deposit boxes and vaults; and computer terminal entry and access to information.

In a typical secured installation there are a limited number of points of entry. In adapting the present invention to such an installation, a terminal will be located at each access site to the installation as well as at the access to any more secure areas within the installation. Each terminal will accept the individual's identification and his fingertip for scanning and will include a means for unlocking a door, activating a one-person-at-a-time turnstile or similar entry device once the computer has determined a match for an authorized inquiry. These remote terminals will be connected to the central computer system by means of a direct cable of twisted pair wiring or the equivalent. The central equipment will be located in a more secure location within the facility and will be made up of a multiplexer, a preprocessor to do parallel image processing operations, and a computer which will do some of the detection and all of the minutiae location and matching functions. If desired, the computer may be directed to give an alarm if there are abnormal patterns of ingress and egress. Disk files coupled to the computer will hold data on any desired number of individuals.

In addition to the basic identification system outlined above, the present invention can be adapted for use in a number of applications. The system can be used in lieu of a time clock, thereby eliminating punching in by proxy. Similarly the system could verify the validity and identity of every person attempting to vote. Since the central processing portion of the system also contains computing and data storage capability, time-in or voting information can be tallied, processed, and stored for further use or displayed. The accuracy of identity verification of which the system is capable makes it ideal for money dispensing systems, or applications such as mass transit ticket systems, where a passenger prepays a given amount and then the price of his ride is deducted from his account each time he uses the system. Since it is the individual which is recognized, not a card or ticket, forgery and black markets in reduced-rate fares can be eliminated. In such a system, the terminals would tend to be many and spread over a relatively large geographical area. Thus, terminal data transmission would most likely be over existing telephone lines using modems, i.e. modulators and demodulators.

BRIEF DESCRIPTION OF THE DRAWINGS

For a fuller understanding of the present invention, reference should now be had to the following detailed description thereof taken in conjunction with the accompanying drawings wherein.

DESCRIPTION OF THE PREFERRED EMBODIMENT

Figure 1:
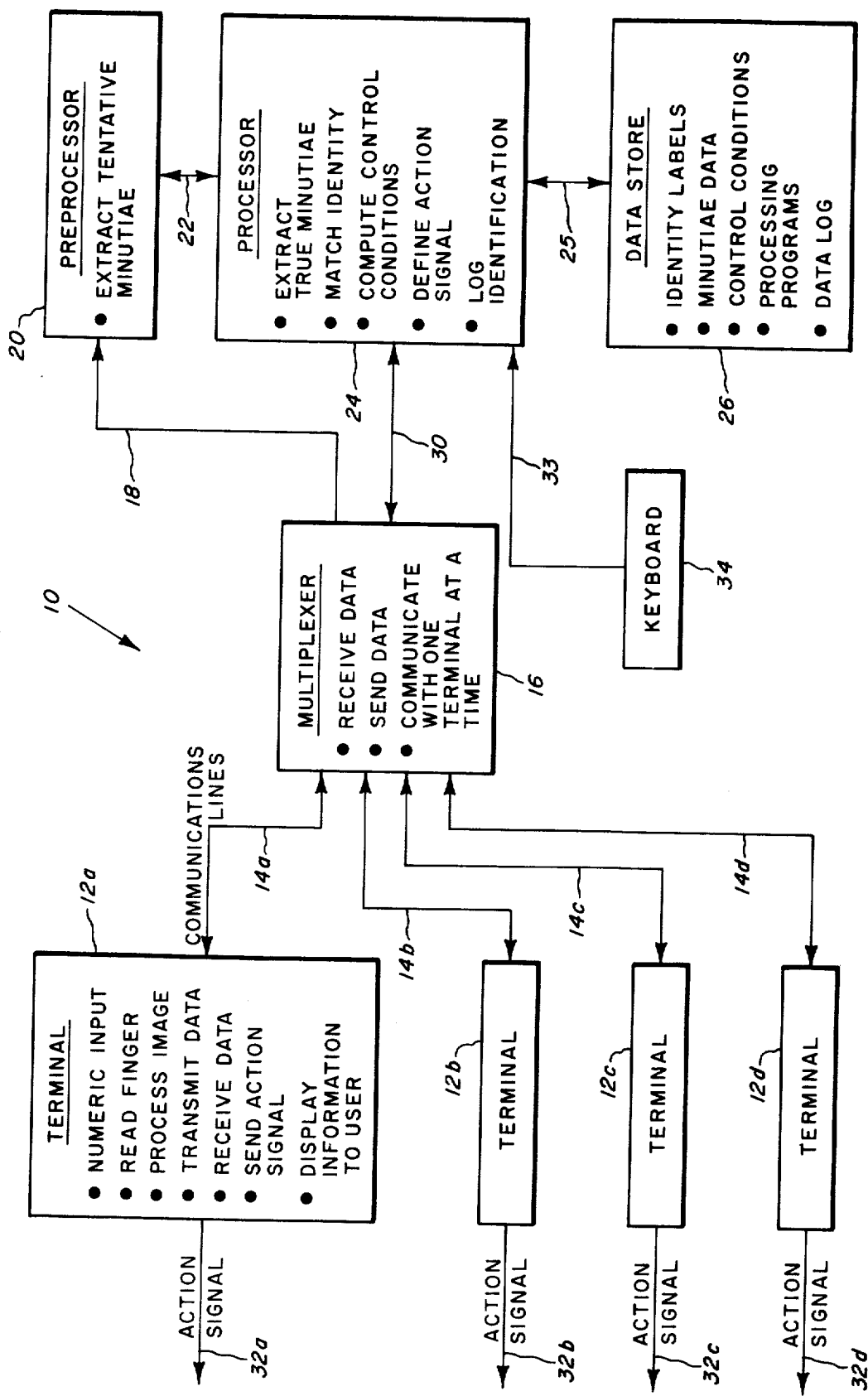
FIG. 1 is a functional block diagram of the system of this invention.

The present invention is best shown in FIG. 1 wherein the numeral 10 generally designates the system. The system 10 consists of one or more terminals of which four have been illustrated and are designated 12a, 12b, 12c and 12d, respectively. Terminals 12a, 12b, 12c and 12d are connected to data multiplexer 16 via communication lines 14a, 14b, 14c and 14d, respectively. The data multiplexer 16 sends fingerprint data from one terminal at a time to a preprocessor 20 via line 18 and sends identity label information to processor 24 via line 30. Preprocessor 20 in turn sends the preprocessed data to processor 24 via line 22. Processor 24 also accesses data store 26 via line 25 for final processing prior to identity verification and action. An action signal, which may cause the opening of a door or the like, is sent to an appropriate device (not illustrated) via lines 32a, 32b, 32c and 32d. As illustrated, the action signal is sent from processor 24 via line 30 to multiplexer 16 and via the appropriate communication line to the terminal which requested the identity verification, however, the action signal can, in appropriate devices, take some other path from the processor 24 to an appropriate device.

The operation of the system of FIG. 1 would be as follows: an individual who wishes to have his identity verified would enter his alleged numeric identity label via a keyboard or card reader on any one of the terminals, e.g. 12a, of the system 10 and would then press the tip of a finger, specified in advance, against the reading window of the terminal 12a. Terminal 12a scans the fingerprint and sends the identity label and a version of the fingerprint on which some electronic signal processing has been performed to accomplish image enhancement to multiplexer 16 via communication line 14a. The multiplexer 16 communicates with only one terminal at a time and leaves any other terminals on "hold" until communication with the one terminal has ended. The multiplexer 16 communicates the alleged identity label to processor 24 via line 30, and processor 24 retrieves the fingerprint minutiae data for that particular person as well as any access conditions associated with his identity from data store 26 via line 25. Multiplexer 16 communicates the processed fingerprint data to preprocessor 20 which extracts all tentative minutiae from it and transmits these tentative minutiae to processor 24 via line 22. Processor 24 further processes the tentative minutiae to extract true minutiae which are then compared with the minutiae on file for the given identity label to check for a match. Depending upon whether a match is declared or not and conditioned by the control data associated with the individual whose identity is to be verified, an action signal is sent back to the terminal 12a by processor 24 via line 30, multiplexer 16 and line 14a. This signal is the ultimate result of the whole process and is supplied to line 32a by terminal 12a and can be used to allow access to a secure area, dispense money, operate an elevator, allow a ride on a public vehicle, etc.

Identity data and minutiae data are added to the data store 26 through essentially the same process as that in which an individual's data is processed for an access attempt. That is, an individual keys in his identity number and his finger is scanned by the terminal 12a. The fingerprint information is processed as previously described through multiplexer 16 preprocessor 20 and processor 24. However, if the processor 24 has previously been set through entry of the individual's identity number and a "create file" code is sent to processor 24 through keyboard 34 via line 33, it transmits the individual's identity data and minutiae data to data store 26 via lines 25 for storage. If the processor 24 receives an identity number and a "delete file" code from keyboard 34 via line 33, it transmits data to the data store 26 over lines 25 to overwrite (erase) the identity data and minutiae data which apply to the individual person.

As outlined above, it is apparent that the system consists of five elements: the terminals (12a, 12b, 12c and 12d); the communications (14a, 14b, 14c and 14d) and multiplexing (16); the preprocessor (20); the processor (24); and the data store (26). These elements will be described in greater detail in the following sections.

TERMINAL

The terminals (12a, 12b, 12c and 12d) have five major functions; (1) to read the fingerprint from a finger placed on the terminal window and present a clean, well-formed binary image of that fingerprint for further processing; (2) to provide the mechanism for quickly and accurately accepting the alleged identity label of an individual requesting identity verification; (3) to provide the means for transmitting the fingerprint binary image and the identity label and for receiving the action signal over the communications system; (4) to provide the means for displaying the states of the terminal and the response from the central processor; and (5) to provide the means for transmitting the action signal to the action device (if such device is located near the terminal).

One of the basic problems in reading fingerprints directly is that the ridges and valleys exhibit poor contrast. In order to produce a good image, the terminals employ an enhancement technique based on the optical phenomenon of total internal reflection as applied to a prism. Light propagating in a prism can be both reflected and refracted at a glass/air boundary and the angles of incidence and refraction and the indices of refraction are related by Snell's law:

$$n_1 \sin \phi_1 = n_2 \sin \phi_2$$

However, there is some critical angle of incidence $\phi_1$ for which $\phi_2 = 90°$. Above this angle, which is about 42° for air and typical compositions of glass, only reflection takes place.

When a finger is placed on the prism surface only the ridges actually make contact with the glass and air pockets are left in the valleys. Thus light incident at the proper angle under the valleys is reflected, while light striking at the ridges will be absorbed in the relatively dense medium of the finger. Sharp images with excellent contrast can be obtained in this fashion.

Figure 2:
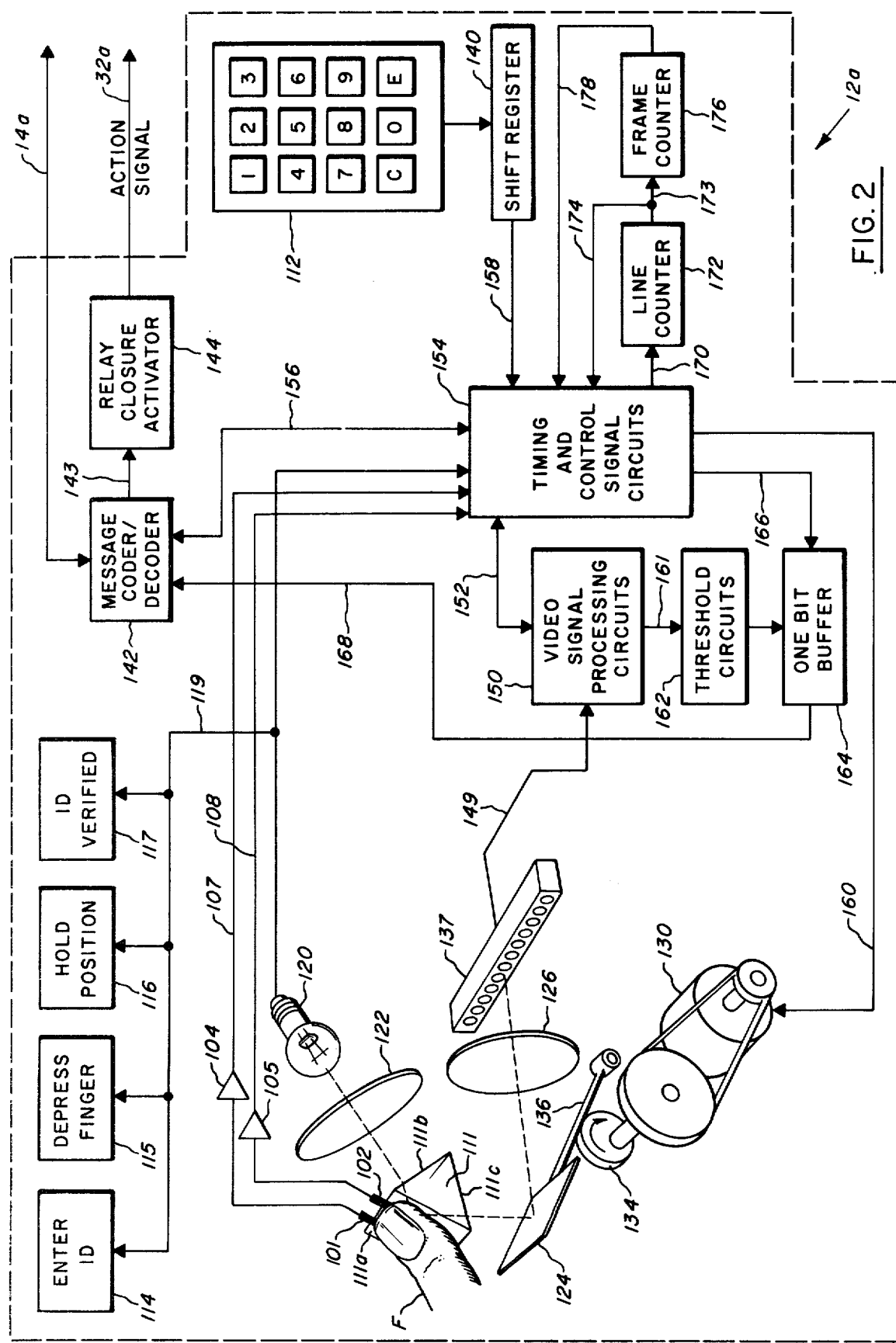
FIG. 2 is a block diagram of a terminal employing a 1-axis scanner.

As shown in FIG. 2, the terminal 12a has a fingerprint scanning window defined by one face 111a of prism 111 for scanning the tip of the finger F, a keyboard 112 for entering an identity label, and a plurality of indicators such as 114–117 for indicating: if the terminal is active and available for identity verification; if the identity label is being verified; if a finger should be placed on the terminal for scanning or rescanning; and if the requested identity has been verified or rejected. Light from the pre-focused lamp 120 is passed through condenser lenses 122 and is directed through face 111b of the object prism 111. Normally this light is all reflected inside the prism 111 and passes on out through face 111c. However, when a subject has placed his finger F on the scanning window defined by face 111a, this reflection is frustrated along the ridges, resulting in a high-contrast black and white pattern. This image is then reflected off the vertical scanning mirror 124 and passed through a multi-element objective lens 126 which focuses this image onto horizontally extending photodetector array 137 and is converted to an electronic television-like raster image by the combination of mechanical and electronic scanning under the control of timing and control signal circuits 154.

The identity label information is generated by keystrokes on keyboard 112 and this data is stored in a shift register 140 and shifted out a character at a time to initiate a verification operation. For communication over telephone lines, the data to be transmitted to the multiplexer 16 is encoded within the terminal 12a in character-like blocks of bits by message coder/decoder 142 for transmission by a modem (not illustrated) via line 14a. The data to be received by the terminal 12a via line 14a from the modem is decoded from character-like blocks of bits by message coder/decoder 142. If terminal 12a is wire connected to the processor 24, line drivers and receivers for the twisted pair (not illustrated) would be included in the terminal 12a. If the requested identity has been verified, the terminal 12a receives a signal from processor 24. The terminal 12a, upon the decoding of the signal by message coder/decoder 142, then makes available to the action device (not illustrated) an action signal via line 143, relay closure activator 144 and line 32a.

OPERATION

Indicator 114 is connected to timing and control signal circuits 154 of terminal 12a via line 119 and indicates that terminal 12a is in the ready state. The person to be identified enters the pertinent identification data on keyboard 112 which transmits the data to shift register 140 which contains a conventional digital electronic shift register circuit. Shift register 140 stores the data transmitted by keyboard 12 and shifts it out one character at a time via line 158 to timing and control signal circuits 154. Timing and control signal circuits 154 contain conventional electronic pulse generators, gating logic circuits and register circuits and transmit the identification data received from shift register 140 to message coder/decoder 142 via line 156. The message coder/decoder 142 contains conventional digital electronic logic circuits and encodes the keyed-in identification data received from timing and control signal circuits 154 for transmission to processor 24 via line 14a, multiplexer 16 and line 30 to determine if the identity exists in data store 26. Additionally, timing and control signal circuits 154 thereupon activate indicator 115 via line 119. In response to indicator 115, the person to be identified places his previously designated finger F on face 111a of prism 111. The correct placing of finger F on prism face 111a causes finger F to contact electrodes 101 and 102 and causes the light which has passed from normally-on, pre-focused lamp 120 through condenser lenses 122 and prism face 111b, to be only partially reflected due to the presence of the ridges of the finger F which are in contact with prism face 111a. The reflected light containing a high-contrast black and white pattern of the fingerprint passes through prism face 111c, is reflected by vertical scanning mirror 124 and passes through multi-element objective lens 126 which focuses the image on the horizontally extending photodetector array 137. The photodetector array 137, which may be a RL-128 series solid state linear scanner manufactured by Reticon Corporation of Mountain View, Calif., produces an output indicative of the pattern of light incident thereon. The output of photodetector array 137 is transmitted via line 149 to video signal processing circuits 150 which include amplifiers, peak detectors and a sample and hold circuit. Signals from electrodes 101 and 102 which are located on prism face 111a of prism 111 are used to detect the presence of finger F in the correct position for a scan to start. These signals are amplified by amplifiers 104 and 105 which are located in lines 107 and 108, respectively, and these amplified signals are used by timing and control signal circuits 154 which in turn send a signal via line 156, message coder/decoder 142, line 14a, multiplexer 16 and line 30 to processor 24 to signal that finger F is in position. An initiation signal is returned to timing and control signal circuits 154 which through a combination of control and feedback signals synchronizes the operation of the elements making up terminal 12a. Because the horizontally extending photodetector array senses a single line of the fingerprint image, the image must be moved across the photodetector array. Movement of the image is accomplished by synchronous motor 130 which starts when the command to start is received from processor 24 and is transmitted to motor 130 via line 160 by timing and control signal circuits 154. Motor 130 is mechanically connected through a pulley, belt, gear train or other suitable connection to drive cam 134 and thereby causes the movement of mirror 124 which is mounted on pivoted member 136 which is in engagement with cam 134. The output of photodetector array 137, which is a series of negative-going pulses of amplitude proportional to the amount of incident light, is fed into video signal processing circuits 150. Video signal processing circuits 150 supply a first output signal to timing and control signal circuits 154 via line 152 and a second output signal, which is a continuous video signal, to threshold circuits 162 via line 161. Threshold circuits 162 includes conventional comparator circuits and a high-pass filter that removes any offset from the video and turns it, in effect, into an alternating current signal. Positive excursions (ridges) and negative excursions (valleys) are distinguished by threshold circuits 162, the output signal from which is clocked into one-bit buffer 164 at the trailing end of the sample pulse as a binary signal. A synchronous control signal is supplied to one-bit buffer 164 via line 166 by timing and control signal circuits 154 and in response thereto transmits the binary signal to message coder/decoder 142 via line 168 for transmission via line 14a, multiplexer 16 and via lines 18 and 30 to preprocessor 20 and processor 24, respectively. Responsive to the output signal supplied via lines 152 to timing and control signal circuits 154, timing and control signal circuits 154 supply an output signal via line 170 to 9-bit counter 172 which includes conventional digital electronic counter circuits. The seven high order bits supplied to counter 172 are used to count up the 128 points that make up a line and supplies an end-of-line signal as an input to frame counter 176 via line 173 and via lines 173 and 174 as a feedback signal to timing and control signal circuits 154. Frame counter 176 which includes conventional digital electronic counter circuits counts up to the 128 lines that make up a complete scan. At that point an end-of-frame signal is fed back to timing and control circuits 154 via line 178 to stop the motor 130 until the next start pulse is received. When all of the identity information has been transmitted to preprocessor 20 and processor 24 and the identity has been verified or challenged an appropriate signal will be transmitted by processor 24 via line 30 multiplexer 16, and communication line 14a to message coder/decoder 142 of terminal 12a. If the identity has been verified, the message coder/decoder 142 will transmit a signal via line 143 to relay closure activator 144. Relay closure activator 144 which is a conventional solid-state or mechanical relay will transmit an action signal via line 32a to open a door, etc. in response to the signal supplied via line 143. Message coder/decoder 142 transmits the identity verification or challenge information to timing and control signal circuits 154 which sends a signal via line 119 to actuate indicator 117 if the identification is verified, or to actuate indicator 116 if the identity is challenged. If the identity is challenged a second scanning of the fingerprint and entry of identification data will be required and an alarm or other appropriate action will be taken if the identity is again challenged.

Figure 3:
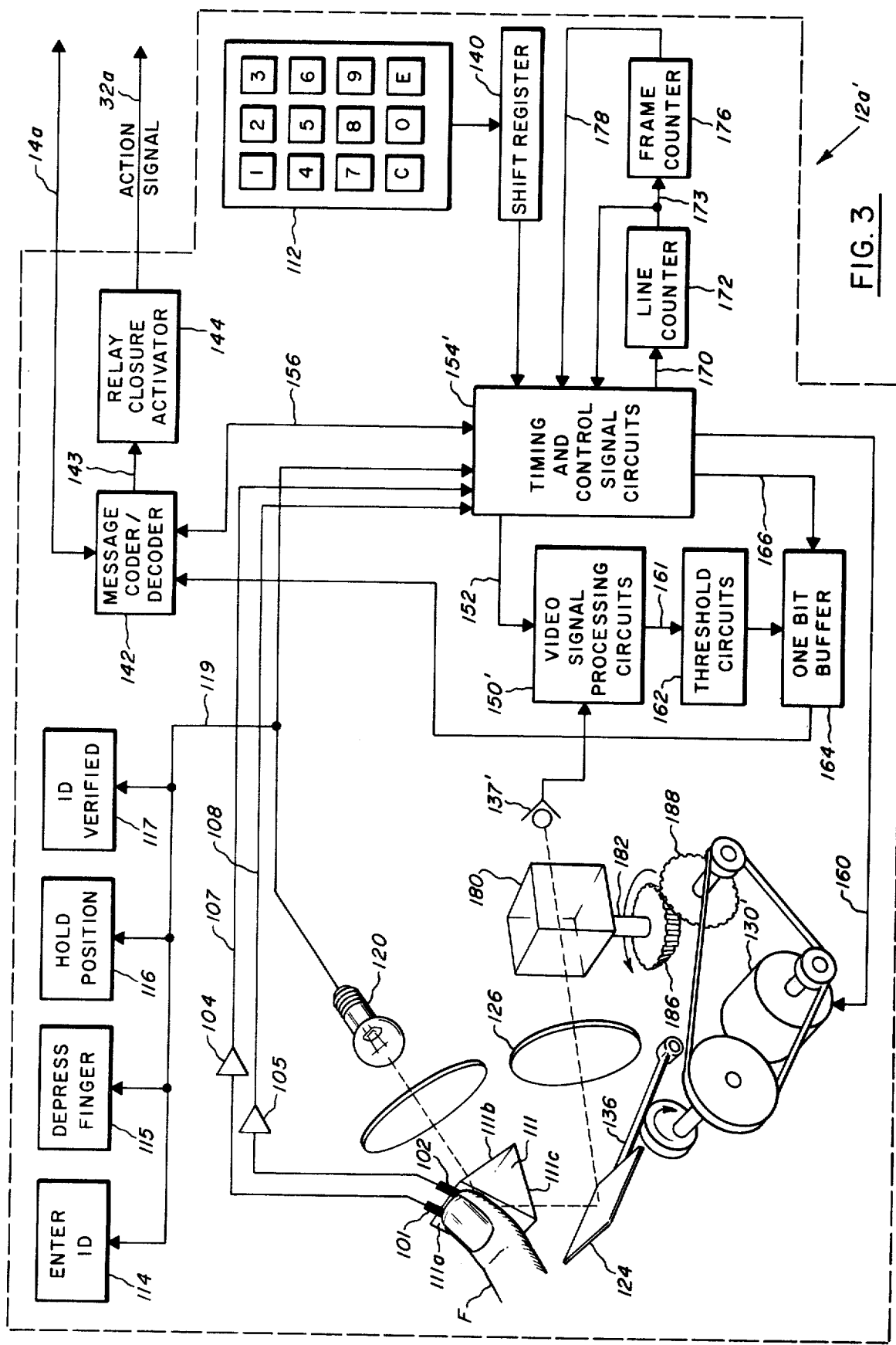
FIG. 3 is a block diagram of a terminal employing a 2-axis scanner.

An alternative terminal configuration 12a' is illustrated in FIG. 3 and primes have been added to the numerals to indicate modified structure. In the 2-axis scanner, the photodetector array 137 of the FIG. 2 device is replaced by a rotating prism 180 of square horizontal cross section and photodetector 137'. Prism 180 is mounted on shaft 182 and is driven by motor 130' through beveled gears 186 and 188 or other suitable connections such as timing belts, pulleys and gear trains. Motor 130' under the control of timing and control signal circuits 154' synchronously drives both pivoted member 136 and shaft 182 to control the movement of both vertical scanning mirror 124 and prism 180. As each face of the prism 180 rotates through the path of the light incident upon it from multi-element objective lens 126, the light is refracted internal to the prism 180 at an angle in the horizontal plane which varies with the angle between the face of the prism 180 and the incident light path direction. The light emerges from the face of prism 180 opposite to that through which it entered, again at a varying angle. As each face of the prism 180 rotates through approximately 90° in the light path, the emerging light scans across the small photodetector 137'. Thus, in effect, a horizontal line or very narrow horizontal strip of the image scans across the photodetector 137'. Since the output of photodetector 137' is continuous, video signal processing circuits 150' need only amplify the signal before feeding it into threshold circuits 162. The structure and operation of terminal 12a' is otherwise identical to that of terminal 12a. A detailed description of a photodetector suitable for use in this application can be found in application Ser. No. 518,442 filed Oct. 29, 1974 and assigned to a common assignee.

COMMUNICATIONS AND MULTIPLEXING

The multiplexer 16 consists of conventional polling circuits and buffer memories and is connected to terminal 12a by communication line 14a which can be either a twisted pair if distances are not too great (less than a few thousand feet) or telephone lines. It is possible to use special communications facilities such as the infrared data links, but these tend to be too expensive except in extraordinary circumstances. If the data link is a twisted pair, conventional integrated circuit driver and receiver circuits can be used, and these would be contained in the terminals and the multiplexer.

When public telephone lines must be used, several choices are available, but in all cases conventional modems must be used between the telephone lines and the terminal of the multiplexer.

The choices with respect to telephone lines have to do with whether the lines will be dial-up, unconditioned leased lines, or conditioned leased lines—in order of increasing expense of line and decreasing time for data transmission. The decision will be made primarily on the basis of cost of communication and the speed at which the data must be communicated between the terminal and the central processor.

The multiplexer 16 serves the function of allowing many terminals to share one preprocessor 20 and processor 24. The relative complexity of the multiplexer 16 depends upon the speed with which the whole system must react to the identification load it must bear. if every other terminal can be made to wait until the terminal presently being serviced by the preprocessor 20 and processor 24 is finished, then the multiplexer 16 can be quite simple. It would be, in effect, a switch connecting the first terminal requesting service into the preprocessor 20 and processor 24. When that transaction was completed it would switch in the next terminal in line which was requesting service. If higher speed operation is required of the system, then the multiplexer 16 may have to take data from every terminal requesting service as fast as each terminal can transmit the data. In this case, the data must be put in a buffer, and, as soon as a buffer is full, that data is sent to the preprocessor 20 and processor 24.

PREPROCESSOR

The preprocessor is a fixed program (wired program) electronic digital computer comprised of conventional digital solid-state integrated-circuit elements including logical gates and registers. The basic function of the preprocessor 20 is to perform a preliminary detection of minutiae from the fingerprint image and the enhancement and organization of the fingerprint image. The preprocessor 20 accepts a serial data stream representative of a digitized (binary) video signal version of the fingerprint which the terminal generates and performs tests on small areas (windows) of the fingerprint image to determine whether a ridge ending or bifurcation (minutiae) exists at the window location and reports detections of candidate minutiae to the processor 24. The two tests performed, which are described in detail below, are the continuity detection logic which determines that a connected ridge extends into but not through the window and the edge test which determines that what extends into the window is a ridge and not a blob. The total allowable scan raster size is 128 points per line. Detection data provided to the processor 24 consists of the X and Y coordinates of the window, a window complement bit, the contents of the window itself and area and perimeter measurements of the candidate minutiae. This data is packed into fourteen 16-bit words and is sent to the processor's input-/output bus by means of data multiplexer 232. Address selection for the data multiplexer 232 is performed by processor 24.

The preprocessor 20 can accept fingerprint image points and contains self-test hardware which allows the processor 24 to perform diagnostic tests to assure the correct operation of the system. Restrictions imposed by both the fingerprint terminals and the processor 24 will reduce the processing rate of the preprocessor 20.

Figure 4:
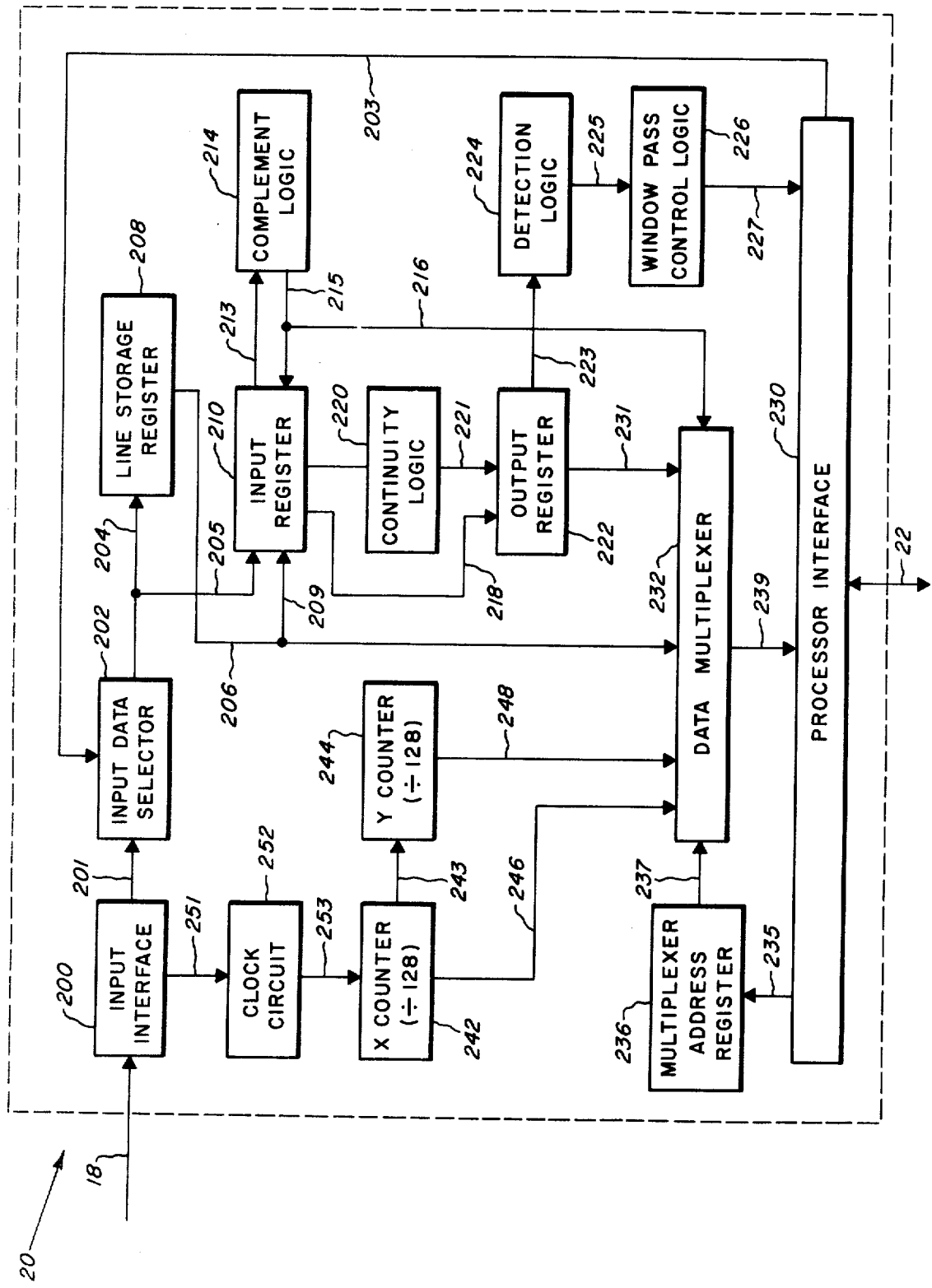
FIG. 4 is a functional block diagram of the preprocessor.

As shown in FIG. 4, the binary data stream is transmitted to preprocessor 20 via line 18 by multiplexer 16 and is received by input interface 200 which is made up of conventional digital electronic logic and register circuits. Input data selector 202 is a gating array made of conventional electronic digital logic circuits that selects the data source for line storage register 208 and input register 210. Line storage register 208 which is made up of eleven 128-bit conventional static shift registers in series in an 11×128 array to provide 1408 bits total storage and input register 210 which is made up of multiple serial in/parallel out shift registers to form a square window array are connected to input data selector 202 via lines 204 and 205, respectively. Normally the data source selected is the fingerprint terminal which is connected to input data selector 202 via line 201, however, under test conditions, the data source is the processor 24 which is connected to input data selector 202 via line 22, processor interface 230 and line 203. Selection of the data source is made through a switch, not illustrated, contained in the input data selector 202 for maintenance purposes. The line storage register 208 provides storage for the eleven previously scanned lines of the fingerprint and, as information from each new point is received, data is shifted through the registers so that the 1408 most recently read points (11 previous lines) are saved. A 12-bit parallel word consisting of the current bit from input data selector 202 and the outputs from the eleven storage registers making up line storage register 208 are supplied via line 205 and via lines 206 and 209, respectively, to form the input word to the input register 210. The input register 210 is the first element in the implementation of a "scanning window" used to examine small areas of the fingerprint for possible detections of fingerprint minutiae. Input register 210consists of multiple serial in/parallel out shift registers whose parallel output terminals at any instant of time comprise a square array of sample points in the sampled fingerprint image. This array also includes logic which can form the bit-wise logical complement of the registers' contents upon demand. The array is loaded, twelve bits at a time, with the word supplied from the line storage register 208 via lines 206 and 209.

Complement logic 214 is made up of conventional digital electronic logic circuits and its purpose is to alter the contents of the input register 210 which are supplied via line 213 so that a ridge ending can be treated like a ridge branch or bifurcation during the subsequent minutiae detection processes. Specifically, this is accomplished by issuing a command via line 215 to form the bit-wise complement of the contents of the input register 210 when certain conditions exist. The conditions regarding the use of the complement are: (1) if either 3 or 4 of the four center points of the array are at logic 1 level the window most probably contains a valley, or possibly a bifurcation, and the array is not complemented; (2) if either 3 or 4 of the four center points of the array are at a logic 0 level the window most probably contains a ridge, or possibly a ridge ending, the array is complemented; and (3) if exactly 2 of the four center points of the array are at a logic 0 level the window probably contains a boundary line of a ridge and a valley, or a smudged area of the print, and the array is complemented only if the previous window was not complemented. Any array that has been complemented is re-complemented before the next data bit from the terminal is accepted. A flag signal is sent to the data multiplexer 232 via line 216 each time a window is complemented.

Continuity logic 220 is made up of a parallel array of conventional digital electronic logic circuits and its purpose is to eliminate, during each cycle of its operation, all points of the image which are contained within the 12×12 window (array) area that are not connected by at least one continuous string of binary image points of logical value "1" to the center four points of the window. These center four points are transferred directly to the output register 222 via line 218. This process eliminates adjacent ridge structure which would tend to obscure detection of candidate minutiae. The continuity logic 220 operates on the image (or complement of the image) contained in the input register 210. The modified image is transferred via line 221 to the output register 222 which provides storage of the binary image point data in the 12×12 window area as modified by the continuity logic 220. The output register 222 consists of twelve 12-bit parallel in/parallel out registers arranged in a 12×12 array and is connected to detection logic 224 and data multiplexer 232 via lines 223 and 231, respectively.

Detection logic 224 is made up of digital electronic logic circuits arranged as conventional counters, registers, adders and gates, the function of which is to perform tests on each window contained in the output register 222 to determine the presence of a possible minutiae. The criteria that a window must meet to be considered as containing a potential minutiae are that: (1) the ridge must not pass completely through the window; and (2) it must not intersect more than a maximum allowable number of resolution elements along the window edge, depending upon its orientation in the window. Windows that meet the above criteria cause the detection logic 224 to generate an acceptance signal to the window pass control logic 226 via line 225.

Window pass control logic 226 is made up of conventional digital electronic gate circuits and its function is to produce a signal which is transmitted via line 227 to processor interface 230 when a potential minutiae detection takes place. Certain other criteria must be met before a report is made to the computer or processor 24. The criteria are: (1) no reports can be made during the first 11 lines of the fingerprint (line lockout); and (2) no reports can be made during the first 11 points of a line (point (lockout). Windows passing the detection logic test and meeting the above criteria will cause the window pass control logic 226 to generate a flag signal to the processor interface 230.

Data multiplexer 232 is made up of digital electronic logic circuits in a conventional multiplexer configuration and its purpose is to access data at particular points in the preprocessor 20 for transfer to the computer or processor 24. Data multiplexer 232 can access a selected, fixed number of multiple-bit words and the address selection for data multiplexer 232 is performed by the processor 24, through line 22, interface 230, line 235, multiplexer address register 236 which is a conventional digital electronic register and line 237. Data from the data multiplexer 232 is passed via line 239, processor interface 230 and line 22 to the processor 24.

All system timing is derived from a conventional 12 phase electronic clock circuit 252 which includes a crystal-controlled oscillator circuit operating at a selected, fixed frequency. Clock circuit 252 is connected to input interface 200 via line 251 and supplies a control signal to X coordinate counter 242 via line 253. Receipt of a timing signal from the terminal initiates the processing cycle. Since system timing is slaved to the terminal data clock circuit 252, no restriction is placed in the data clock rate other than that it must not occur faster than the processing rate of the preprocessor 20 and that exactly 16,384 pulses must occur for each scan of a fingerprint. Detection of an end-of-print signal disables the preprocessor 20 and enabling occurs by a command from the processor 24.

X and Y coordinate counters 242 and 244 are made up of conventional digital electronic counter circuits whose purpose is to indicate the X and Y coordinates of the point being processed during the scan of the fingerprint. The X-counter 242 is 7 bits long and counts 128 positions along a line. The Y-counter 244 which is 7 bits long and counts 128 lines is connected to X-counter 242 via line 243 and thereby to clock circuit 252. Full count of both the X and Y counters 242 and 244 will generate an end-of-print flag to processor 24 via lines 246 and 248, respectively, data multiplexer 232, line 239, processor interface 230 and line 22.

The processor interface 230 which is made up of conventional digital electronic logic circuits arranged as gates is not physically a part of the preprocessor 20. The function of interface 230 is to provide processor control of the preprocessor 20 and to facilitate transfers of data to and from the processor 24. Processor interface 230 generates a start signal to enable the preprocessor 20. As preprocessor 20 detects candidate minutiae it signals the processor 24 which then addresses the data multiplexer 232 and reads the detection parameters.

In the test mode, processor 24 generates test patterns via line 22 and through the processor interface 230 which supplies them to input data selector 202 via line 203. Preprocessor 20 operates on the test patterns and the results are read back through processor interface 230 for analysis by the processor 24. A determination of proper operation of the preprocessor can then be made.

CENTRAL PROCESSOR

The processor 24 is a conventional miniature electronic digital computer having suitable capability for high-speed processing of digital sampled data and control of external devices and performs the following programmed functions: (1) perform more stringent tests upon the minutiae sent by the preprocessor 20 to eliminate any duplicate minutia detections or any non-minutiae passed by the preprocessor 20; (2) eliminate false minutiae caused by scars, creases, breaks in ridges due to a poor image or pores, and edge effects; (3) determine the minutia angle; (4) send the alleged identity label data to the data store 26 and thereafter receive a corresponding set of minutiae data from the data store 26; (5) match the minutiae sent by the terminal with the minutiae retrieved from the data store 26 associated with the identity label sent by the terminal; (6) if the match test verifies the identity, determine if other conditions preclude positive action; (7) if all conditions are favorable send the action signal to the requesting terminal; (8) send an alarm if conditions warrant; (9) log the identity verification request; (10) adaptively improve the reference minutiae list for each identity whenever an identity is verified; (11) perform self tests to determine that the systen is functioning correctly; and (12) perform other utility functions such as computing the new balance of a subscriber who has used his credit for some reason or compute the number of voters voting for and against some measure.

DATA STORE

The data store 26 consists of a conventional direct-access storage device such as a magnetic disk memory device as is conventional in the electronic data processing art. It also includes conventional timing and control circuits which cause synchronous transfer of data from the store to processor 24 when a command is issued from the processor 24.

The specific details of the embodiments of the present invention will depend upon the specific application for which it is intended. Factors which will influence the ultimate choice of a system for a specific application will include the number of terminals, the location (near or remote) of the terminals, the types of terminals (such as those controlling entry of more secure areas), the number of persons to be permitted entry, the rate of entry, the data to be recorded (time clock, service usage, fingerprint data of person seeking unauthorized entry, etc.), the acceptable probability of denying access to authorized persons, the acceptable probability of permitting access by unauthorized persons, etc. While the ultimate solution will depend upon the parameters dictated by the specific use, the principles applied in formulating the specific electronic circuits making up the described components will be those that are conventional in the art as exemplified by the standard references "Arithmetic Operations in Digital Computers" by R. K. Richards, "Digital Circuits and Devices" by Teuvo Kohonen and "The Design of Digital Systems" by John B. Peatman, "Integrated Circuits in Digital Electronics" by Arpad Barna and Dan I. Porat, "Multiprocessors and Parallel Processing" edited by Philip H. Enslow, Jr., and "Design of Digital Computers" by Hans W. Gschwind and Edward J. McCluskey.

Although preferred embodiments of the present invention have been illustrated and described, other changes will occur to those skilled in the art. For example, additional indicators may be employed in the terminals and the identification number may be on a card which is inserted into the terminal. The area and resolution of scanning may change to match the specific accuracy requirements of a given application. Additional information may be required to be keyed in by a terminal user to either expedite a more complex transaction or to further establish the nature of his access objective. Other conventional methods may be used for implementing a 2-dimensional raster scan of the fingerprint image area such as the use of a 2-dimensional electro-optical sensor array. Two synchronous or directly coupled motors may be used in place of belt and gear drives. Also, the entire unit can be self contained for appropriate uses. It is therefore intended that the scope of the present invention is to be limited only by the scope of the appended claims.

We claim:

1. Terminal means for reading fingerprints and for transmitting and receiving data and including:
    (a) means for displaying information to a user;
    (b) means for entering identity data;
    (c) prism means having one face to be contacted by a finger of a person to be identified;
    (d) photodetector means for producing an electrical output directly related to light incident thereon;
    (e) means for projecting an image of a fingerprint, of a finger of the person to be identified which is in contact with said prism means, onto said photodetector means;
    (f) means for moving the image of the fingerprint of the person to be identified across said photodetector means;
    (g) video signal processing means for processing the electrical output of said photodetector means;
    (h) means for synchronizing said means for moving an image and said video signal processing means;
    (i) means for transmitting entered identity data and the processed electrical output of said photodetector means; and
    (j) means for receiving data indicating whether an identity is confirmed.

2. The terminal means of claim 1 wherein said photodetector means is a horizontally extending array.

3. The terminal means of claim 1 wherein said means for projecting an image of a fingerprint includes a rotating prism.

4. Preprocessor means for receiving fingerprint data, for testing portions of the received fingerprint data to tentatively determine the presence of minutiae, for identifying the portions of the tested fingerprint data containing tentative minutiae and for transmitting the identified portions of the fingerprint data to processor means for further testing and including:
    means for receiving a serial, binary data stream representative of a digitized fingerprint image;
    means for performing tests on small areas of said digitized fingerprint image defining windows to determine the presence of tentative minutiae at the window locations;
    means for identifying the windows containing tentative minutiae; and
    means for transmitting each window containing tentative minutiae in the form of the X and Y coordinates of said windows, window complement bits and the contents of said windows to said processor means.

* * * * *